United States Patent
Omatsu et al.

Patent Number: 5,414,138
Date of Patent: May 9, 1995

[54] PROCESS FOR PRODUCING 2-FORMYL-1,4-BUTANEDIOL

[75] Inventors: Toshihiro Omatsu, Kamisu; Yasuo Tokitoh, Hasaki, both of Japan

[73] Assignee: Kuraray Company Ltd., Kurashiki, Japan

[21] Appl. No.: 253,276

[22] Filed: Jun. 2, 1994

[30] Foreign Application Priority Data

Jun. 2, 1993 [JP] Japan .................... 5-156183

[51] Int. Cl.$^6$ .................... C07C 45/50; C07C 27/00
[52] U.S. Cl. .................... 568/454; 568/451; 568/862; 568/865
[58] Field of Search ........... 568/454, 451, 865, 862

[56] References Cited

U.S. PATENT DOCUMENTS

| | | | |
|---|---|---|---|
| 3,859,369 | 1/1975 | Copelin | 568/454 |
| 4,201,728 | 5/1980 | Hughes . | |
| 4,238,419 | 12/1980 | Matsumoto et al. | 568/454 |
| 4,420,640 | 12/1983 | Matsumoto et al. | 568/454 |
| 4,467,116 | 8/1984 | van Leeuwen et al. | 568/454 |
| 4,510,332 | 4/1985 | Matsumoto et al. | 568/454 |
| 4,537,997 | 8/1985 | Kojima et al. . | |
| 4,663,468 | 5/1987 | Tokitoh et al. | 549/273 |
| 4,808,737 | 2/1989 | Yoshimura et al. | 549/423 |
| 4,861,922 | 8/1989 | Tokitoh et al. | 568/451 |
| 5,012,006 | 4/1991 | Bertleff et al. | 568/451 |

FOREIGN PATENT DOCUMENTS

| | | |
|---|---|---|
| 0303060 | 2/1989 | European Pat. Off. . |
| 2428021 | 1/1980 | France . |
| 2014138 | 8/1979 | United Kingdom . |

*Primary Examiner*—Werren B. Lone
*Attorney, Agent, or Firm*—Oblon, Spivak, McClelland, Maier & Neustadt

[57] ABSTRACT

A process for producing 2-formyl-1,4-butanediol comprises effecting reaction of 2-butene-1,4-diol with hydrogen and carbon monoxide in the presence of:

(a) a rhodium compound, (b) a tris(substituted aryl) phosphite having an electronic parameter, $\nu$-value, of 2,080 to 2,090 cm$^{-1}$ and a steric parameter, $\theta$-value, of 135° to 190° and being represented by the formula $P(OR)_3$ wherein each of R's, which may be the same or different, represents a substituted aryl group having at least 7 carbon atoms, and (c) a bis (diphenylphosphino) alkane represented by the formula $Ph_2P\text{-}(CH_2)_n\text{-}PPh_2$ where n n is an integer of 2 to 6, and at a temperature of not more than 80° C.

10 Claims, No Drawings

PROCESS FOR PRODUCING 2-FORMYL-1,4-BUTANEDIOL

BACKGROUND OF THE INVENTION

1. Field of the Invention

The present invention relates to a process for producing 2-formyl-1,4-butanediol by hydroformylating 2-butene-1,4-diol by reaction with hydrogen and carbon monoxide in the presence of a catalyst. 2-Formyl-1,4-butanediol can be introduced, upon hydrogenation, into 2-methylol-1,4-butanediol, which is valuable as a starting material for polymers such as polyesters, as well as medicines, and, upon oxidation, into 2-carboxy-1,4-butanediol, which is useful as a starting material for polymers such as polyurethanes.

2. Description of the Related Art

Reaction of olefinically unsaturated organic compounds with hydrogen and carbon monoxide to obtain aldehydes, called hydroformylation or oxo-reaction, is known as an industrially valuable synthesis process. For this reaction, catalysts of cobalt compounds or rhodium compounds are generally used. In particular, rhodium compounds are well known as being superior to cobalt compounds in the catalytic activity for hydroformylation and the selectivity for the resulting aldehydes. However, rhodium carbonyl is unstable and hence used in forms modified with a ligand containing phosphorous, arsenic or antimony, among which organic phosphorous compounds such as triphenyl phosphine are preferably used.

Butenediol is readily obtainable by partial hydrogenation of butynediol, which is manufactured from acetylene by Reppe reaction on a large scale. Butenediol can also be obtained by hydrolyzing diacetoxy-2-butene, which is synthesized from butadiene.

U.S. Pat. No. 3,859,369 discloses hydroformylation of butenediol by using a catalyst of rhodium or the like with a ligand of a phosphine.

It is, however, difficult to achieve a high yield in obtaining the desired compound of 2-formyl-1,4-butanediol in accordance with the process disclosed in U.S. Pat. No. 3,859,369. This is because that the reaction in this process necessarily causes 4-hydroxy-2-methylenebutylaldehyde in a considerably large amount or that the reaction itself terminates midway to cause a large amount of the starting material butenediol to remain unreacted.

While it is necessary, in order to obtain the desired 2-formyl-1,4-butanediol in a high yield, to maintain the reaction temperature at a low level, the use of a phosphine as described in this U.S.P. then results in a markedly low reaction rate. For the purpose of avoiding the above problems and achieving a satisfactory reaction rate on an industrial basis, it may be considered to use a large amount of a rhodium catalyst. Since rhodium catalysts are very expensive, their use in a large amount would be uneconomical unless they are recovered and repeatedly reused for a long period of time.

U.S. Pat. No. 4,467,116 and Japanese Patent Application Laid-open No. 123134/1982 disclose a process for the hydroformylation of olefinically unsaturated compounds which comprises the use of a rhodium catalyst modified with a phosphite that can give a very high reaction rate. This process has the advantage of achieving a high reaction rate, whereby the rhodium compound can be used only in a small amount even when the reaction is effected at low temperatures and thus the problem of economy is minimized. However, even with the use of this type phosphite to effect the hydroformylation of 2-butene-1,4-diol while maintaining a low reaction temperature, the severe problem of the reaction terminating midway at a low conversion of the starting material, although the initial reaction rate is high.

SUMMARY OF THE INVENTION

Accordingly, an object of the present invention is to provide a process for producing 2-formyl-1,4-butanediol by hydroformylating butenediol in a high yield and economically with a small amount of rhodium catalyst, while achieving an industrially satisfactory reaction rate.

As a result of an intensive study to achieve the above object, the present inventors have completed the invention.

Thus, the present invention provides a process for producing 2-formyl-1,4-butanediol which comprises effecting reaction of 2-butene-1,4-diol with hydrogen and carbon monoxide in the presence of:

(a) a rhodium compound, (b) a tris(substituted aryl) phosphite having an electronic parameter, $\nu$-value, of 2,080 to 2,090 $cm^{-1}$ and a steric parameter, $\theta$-value, of 135 to 190° and being represented by the formula $P(OR)_3$ wherein each of R's, which may be the same or different, represents a substituted aryl group having at least 7 carbon atoms, and (c) a bis (diphenylphosphino) alkane represented by the formula $Ph_2P\text{-}(CH_2)_n\text{-}PPh_2$ wherein n is an integer of 2 to 6; and at a temperature of not more than 80° C.

DETAILED DESCRIPTION OF THE PREFERRED EMBODIMENTS

In the present invention, the above 2 parameters are those defined by C. A. Tolman (Chem. Rev., 177, 313 (1977)), and the electronic parameter is the frequency of the A1 infrared absorption spectrum of CO in an Ni(CO)$_3$L, wherein L is a ligand, measured in dichloromethane, and the steric parameter is defined by the apex angle of a cylindrical cone, centered 2.28 Å from the center of the phosphorous atom, which just touches the van der Waals radii of the outermost atoms contained in the groups bonded to the phosphorous atom.

The tris(substituted aryl) phosphite used in the present invention is represented by formula $P(OR)_3$, wherein each of the three R's, which may be the same or different, means a substituted aryl group having at least 7 carbon atoms. The number of carbon atoms has no specific upper limit. The aryl group may be substituted with any group as long as it does not hinder the hydroformylation. Examples of the phosphite are tris(2-methylphenyl) phosphite, tris(2,6-dimethylphenyl) phosphite, tris(2-isopropylphenyl) phosphite, tris(2-phenylphenyl) phosphite, tris(2-t-butylphenyl) phosphite, tris(2,4-di-t-butylphenyl) phosphite, tris(2-t-butyl-5-methylphenyl) phosphite, tris(2-methyl-4-chlorophenyl) phosphite, di(2-methylphenyl)(2-t-butylphenyl) phosphite, di(2-t-butylphenyl)(2-methylphenyl) phosphite, and mixtures of the foregoing, among which tris(2-t-butylphenyl) phosphite, tris(2-t-butyl-5-methylphenyl) phosphite, tris(2,4-di-t-butylphenyl) phosphite and mixtures thereof are particularly preferred for industrial production.

The rhodium compound used in the hydroformylation reaction according to the present invention includes any rhodium compound that has a catalytic activity for hydroformylation or can so change as to have catalytic activity for hydroformylation under the employed hydroformylation reaction conditions. Examples of the compound are $Rh_4(CO)_{12}$, $Rh_6(CO)_{16}$, $Rh(acac)(CO)_2$, rhodium oxide, rhodium chloride, rhodium acetylacetonate and rhodium acetate. In the present invention, these rhodium compounds exhibit markedly high catalytic activity and it is recommended to use for the reaction one in a low concentration of 0.02 to 0.25 mg-atom/liter as converted into rhodium atom.

The tris(substituted aryl) phosphite is used desirably in a concentration of 20 to 500 molar equivalents per 1 gram atom of rhodium. With concentrations below 20 molar equivalents the selectivity to hydroformylation tends to decrease, while with concentrations exceeding 500 molar equivalents the reaction rate tends to decrease.

The bis (diphenylphosphino) alkane used in the present invention is represented by formula $Ph_2P\text{-}(CH_2)_n\text{-}PPh_2$, wherein n is an integer of 2 to 6, and its examples include bis(diphenylphosphino)ethane, bis (diphenylphosphino)propane, bis(diphenylphosphino)butane and bis (diphenylphosphino)pentane.

The bis(diphenylphosphino)alkane is used desirably in a concentration of 0.1 to 5 molar equivalents per 1 gram atom of rhodium, more preferably in a concentration of 0.1 to 2 molar equivalents on the same basis. With the concentration being less than 0.1 molar equivalent, the reaction rate tends to decrease of the reaction stops midway; and with the concentration exceeding 5 molar equivalents the reaction rate also tends to decrease.

The reaction temperature employed in the hydroformylation of the present invention is not more than 80° C, preferably in a range of 20° to 70° C. If the reaction temperature is less than 20° C, the reaction rates will tend to become low. If the reaction temperature exceeds 80° C, the reaction will tend to terminate midway.

In the mixed gas of hydrogen and carbon monoxide used in the reaction, the molar ratio between the two, hydrogen/carbon monoxide, is generally selected from the range of feed gas composition of ½ to 5/1. The reaction pressure is, depending on the reaction temperature though, generally selected from the range of 60 to 200 atmospheres. With the pressure being lower than 60 atmospheres, the selectivity to hydroformylation decreases. It is industrially advantageous, in view of equipment and operation, to maintain the reaction pressure at not more than 200 atmospheres. The reaction may be carried out either continuously or batchwise, in a stirred tank reactor or a bubble column reactor.

It is desirable to carry out the hydroformylation according to the present invention in a solvent that can act to increase the solubility of the rhodium compound, tris (substituted aryl) phosphite and bis (diphenylphosphino)-alkane and is inactive in the reaction zone. Examples of this type solvents are alcohols, e.g. methanol, ethanol, propanol, butanol, n-octanol and ethylene glycol; saturated aliphatic hydrocarbons, e.g. hexane, heptane and octane; aromatic hydrocarbons, e.g. benzene, toluene, xylene, cumene, pseudecumene and ethylbenzene; glycol dimethyl ethers, e.g. ethylene glycol dimethyl ether, diethylene glycol dimethyl ether and triethylene glycol dimethyl ether; esters, e.g. ethyl acetate and dioctyl phthalate; ethers, e.g. tetrahydrofuran and dioxane; and mixtures of the foregoing.

The solvent is used preferably in an amount of at least 10% by volume of the reaction liquid, more preferably in a range of 20 to 50% by volume.

In the reaction of the present invention, the starting material and the reaction product being an alcohol and an aldehydes, respectively, it often occurs that part of the product is acetalized, which tendency enhances with an alcohol solvent. This tendency is suppressed by addition of an organic tertiary amine. The organic tertiary amine is used preferably in a concentration in the reaction liquid of 2 to 50 mmoles/liter. Examples of usable organic tertiary amines are aliphatic alkyl tertiary amines, e.g. triethylamine, tributylamine and tri-n-octylamine; alkyl-substituted tertiary diamines, e.g. N,N,N',N'-tetramethyl-1,2-diaminoethane, N,N,N',N'-tetramethyl-1,3-diaminopropane and N,N,N',N'-tetramethyl-1,4-diaminobutane; tertiary alkanolamines, e.g. N,N-diethylethanolamine and triethanolamine; alicyclic tertiary amines, e.g. N-methylpiperidine, N-methylpyrrolidine and N-methylmorphorine and cyclic unsaturated tertiary amines, e.g. pyridine and picoline.

Where the solvent used in the hydroformylation process according to the present invention is water insoluble, the hydroformylated product can be separated from the catalyst components used by extracting the product with water from the reaction mixture. Upon this extraction, there are formed 2 layers of a water phase containing 2-formyl-1,4-butanediol and an organic layer containing the catalyst components used comprising the rhodium compound, tris(substituted aryl) phosphite and bis(diphenylphosphino)alkane.

Preferred examples of usable water insoluble solvents in conducting the extraction separation with water are n-octanol, benzene, toluene, xylene and mixtures of the foregoing. For this extraction, it is desirable to use water in an amount of at least 30% by volume based on the reaction liquid. Although the amount of water has no specific upper limit, it is not economical to use as large a volume of water as at least 2 times that of the reaction liquid. The extract layer can be, as it is containing water, subjected to hydrogenation, oxidation or like succeeding reactions, or can be distilled to obtain 2-formyl-1,4-butanediol. It is also possible, in order to recover trace amounts of catalyst components contained in the extracted water layer, to contact it with an aromatic hydrocarbon such as toluene to extract the catalyst components into the organic layer. The raffinate forming the organic layer can, as it is, be circulated to the reaction vessel, thereby reusing the catalysts in an active state. This is economical since rhodium catalysts are very expensive.

EXAMPLES

Other features of the invention will become more apparent in the course of the following descriptions of exemplary embodiments which are given for illustration of the invention and are not intended to be limiting thereof.

EXAMPLE 1

A 300-ml autoclave equipped with a gas inlet, a sampling port and an electromagnetic stirrer was charged, while care was taken to avoid contact with air, with 2.58 mg (0.01 mmole) of rhodium dicarbonylacetylacetonate, 208 mg of tris(2-t-butyl-5-methylphenyl) phosphite, 2.13 mg (0.005 mmole) of bis (diphenylphosphino) butane, 149 mg of triethanolamine, 10 ml of toluene, 20 ml of n-octanol and 70 ml (25° C.) of 2-butene-1,4-diol, and the inside of the autoclave was kept under a pressure of 100 kg/cm$^2$ G with a 3/1 mixed gas of hydrogen/carbon monoxide. Stirring of the contents was started at a rate of 1,000 rpm, while the off-gas was withdrawn at 30 l/h. The inside temperature was elevated up to 55° C. over 20 minutes and reaction was effected under these conditions for 8 hours. The conversion was 95% and the selectivity to hydroformylation was 87%.

COMPARATIVE EXAMPLE 1

Example 1 was repeated except that 2.13 mg of the bis(diphenhylphosphino)butane was not added. The conversion was 16% and the selectivity to hydroformylation was 92%.

EXAMPLE 2

A 300-ml autoclave equipped with a gas inlet, a sampling port and an electromagnetic stirrer was charged, while care was taken to avoid contact with air, with 3.87 mg (0.015 mmole) of rhodium dicarbonylacetylacetonate, 390 mg of tris(2-t-butyl-5-methylphenyl) phosphite, 2.556 mg (0.006 mmole) of his (diphenylphosphino) butane, 224 mg of triethanolamine, 15 ml of toluene, 60 ml of triethylene glycol dimethyl ether and 75 ml (25° C.) of 2-butene-1,4-diol, and the inside of the autoclave was kept under a pressure of 90 kg/cm$^2$G with a 2/1 mixed gas of hydrogen/carbon monoxide. Stirring of the contents was started at a rate of 1,000 rpm, while the off-gas was withdrawn at 30 l/h. The inside temperature was elevated up to 50° C. over 30 minutes and reaction was effected under these conditions for 6 hours. The conversion was 94% and the selectivity to hydroformylation was 88%.

COMPARATIVE EXAMPLE 2

Example 2 was repeated except that 197 mg (0.75 mmole) of triphenylphosphine was used instead of 30 mg of the tris (2-t-butyl-5-methylphenyl) phosphite was not added. The conversion was 21% and the selectivity to hydroformylation was 97%.

EXAMPLE 3

A 300-ml autoclave equipped with a gas inlet, a sampling port and an electromagnetic stirrer was charged, while care was taken to avoid contact with air, with 3.87 mg (0.015 mmole) of- rhodium dicarbonylacetylacetonate, 969 mg of tris(2,4-di-t-butylphenyl) phosphite, 5.112 mg (0.012 mmole) of bis (diphenylphosphino) butane, 112 mg of triethanolamine, 15 ml of toluene, 60 ml of triethylene glycol dimethyl ether and 75 ml (25° C.) of 2-butene-1,4-diol, and the inside of the autoclave was kept under a pressure of 120 kg/cm$^2$G with a 1/1 mixed gas of hydrogen/carbon monoxide. Stirring of the contents was started at a rate of 1,200 rpm, while the off-gas was withdrawn at 10 l/h. The inside temperature was elevated up to 50° C. over 30 minutes and reaction was effected under these conditions for 9 hours. The conversion was 94% and the selectivity to hydroformylation was 90%.

COMPARATIVE EXAMPLE 3

Example 3 was repeated except that 465 mg (1.5 mmoles) of triphenyl phosphite was used instead of 969 mg of the tris(2,4-di-t-butylphenyl) phosphite was not added. The conversion was 40% and the selectivity to hydroformylation was 92%.

EXAMPLE 4

A 300-ml autoclave equipped with a gas inlet, a sampling port and an electromagnetic stirrer was charged, while care was taken to avoid contact with air, with 2.58 mg (0.01 mmole) of rhodium dicarbonylacetylacetonate, 208 mg of tris(2-t-butyl-5-phenyl) phosphite, 2.13 mg (0.005 mmole) of bis(diphenylphosphino)butane, 1 85 mg of tri-n-octylamine, 10 ml of toluene, 20 ml of n-octanol and 70 ml (25° C.) of 2-butene-1,4-diol, and the inside of the autoclave was kept under a pressure of 90 kg/cm$^2$G with a 3/1 mixed gas of hydrogen/carbon monoxide. Stirring of the contents was started at a rate of 1,000 rpm, while the off-gas was being flown at 30 l/h. The inside temperature was elevated up to 50° C. over 30 minutes and then reaction was effected under this condition for 12 hours. The conversion was 95% and the selectivity to hydroformylation was 86%. After completion of the reaction, the reaction mixture was cooled to room temperature and then wholly transferred, under an atmosphere of nitrogen, into a 300-ml separating funnel, to which 50 ml of water was added. After mixing by stirring, the mixture was separated. The upper organic layer was, together with 70 ml (25° C.) of 2-butene-1,4-diol fed to a 300-ml autoclave equipped with a gas inlet, a sampling port and an electromagnetic stirrer, while care was taken to avoid contact with air. The inside was kept under a pressure of 90 kg/cm$^2$G with a 3/1 mixed hydrogen/carbon monoxide. Reaction was effected again under the same condition as used in the first reaction. The conversion was 82% and the selectivity to hydroformylation was 86%.

REFERENCE EXAMPLE

After completion of the second reaction of Example 4 above, the reaction mixture was, in the same manner as after the first reaction of Example 4, cooled to room temperature and wholly transferred to a 300-ml separating funnel under an atmosphere of nitrogen, to which 50 ml of water was then added. After being stirred, the mixture was separated and a water phase was obtained from the bottom layer. To the water phase there was combined the water phase remaining after the first reaction was added. Water was further added to the resulting water phase to make 300 ml of an aqueous solution.

A 1-liter autoclave was charged, under nitrogen, with the aqueous solution thus obtained. To the contents 70 g of Raney nickel was added, and then the gas in the autoclave was replaced by hydrogen. Reaction was effected at 50° C. for 7 hours while the pressure was maintained at 9 kg/cm$^2$. The temperature was then raised to 80° C. under the same pressure and reaction was further effected for 7 hours. After completion of the reaction, the reaction mixture was cooled and then filtered to remove the catalyst. The filtrate was treated in an evaporator to remove off water. The residue was subjected to vacuum distillation to give 130 g of 2-methylol-1,4-butanediol.

Obviously, numerous modifications and variations of the present invention are possible in light .of the above teachings. It is therefore to be understood that within the scope of the appended claims, the invention may be practiced otherwise than as specifically described herein.

What is claimed is

1. A process for producing 2-formyl-1,4-butanediol which comprises effecting reaction of 2-butene-1,4-diol with hydrogen and carbon monoxide in the presence of:
   (a) a rhodium compound,
   (b) a tris(substituted aryl) phosphite having an electronic parameter, $\nu$-value, of 2,080 to 2,090 cm$^{-1}$ and a steric parameter, $\theta$-value, of 135° to 190° and being represented by the formula P(OR)$_3$
   wherein each of R's, which may be the same or different, represents a substituted aryl group having at least 7 carbon atoms, and
   (c) a bis(diphenylphosphino)alkane represented by the formula Ph$_2$P-(CH$_2$)n-PPh$_2$ wherein n ms an integer of 2 to 6; and at a temperature of not more than 80° C.

2. The process according to claim 1, wherein said tris(substituted aryl) phosphite is a compound selected from the group consisting of tris(2-t-butylphenyl) phosphite, tris (2-t-butyl-5-methylphenyl) phosphite and tris (2,4-di-t-butylphenyl) phosphite.

3. The process according to claim 1, wherein said bis(diphenylphosphino)alkane is a compound selected from the group consisting of bis(diphenylphosphino)ethane, bis(diphenylphosphino)propane, bis(diphenylphosphino)butane and bis(diphenylphosphino)pentane.

4. The process according to claim 1, wherein said reaction is effected with said rhodium compound in a concentration as converted into rhodium atom of 0.02 to 0.25 mg-atom/liter in combination with said tris(substituted aryl) phosphite in an amount of 20 to 500 moles per 1 g-atom of rhodium and under a pressure of 60 to 200 atmospheres.

5. The process according to claim 1, wherein said reaction is effected in the presence of an organic tertiary amine.

6. The process according to claim 5, wherein said organic tertiary amine is an aliphatic alkyl tertiary amine, an alkyl-substituted tertiary diamine, a tertiary alkanolamine, an alicyclic tertiary amine or a cyclic unsaturated tertiary amine.

7. The process according to either claim 5 or claim 6, wherein the concentration of said organic tertiary amine in the reaction liquid is in a range of 2 to 50 mmoles/liter.

8. The process according to claim 1, wherein said reaction is effected in the presence of a water insoluble solvent, the reaction products are extracted with water from the obtained reaction mixture and the raffinate organic layer is circulated for re-use to said reaction of 2-butene-1,4-diol with hydrogen and carbon monoxide.

9. The process according to claim 8, wherein said water insoluble solvent is n-octanol, benzene, toluene, xylene or a mixture of the foregoing.

10. A process for producing 2-methylol-1,4-butanediol, which comprises hydrogenating the 2-formyl-1,4-butanediol produced by the process of claim 1.

* * * * *

UNITED STATES PATENT AND TRADEMARK OFFICE
CERTIFICATE OF CORRECTION

PATENT NO. : 5,414,138

DATED : May 9, 1995

INVENTOR(S) : OMATSU ET AL

It is certified that error appears in the above-identified patent and that said Letters Patent is hereby corrected as shown below:

Title page, item [57], col. 2,
In the Abstract, , third line from the end, "where n" should be --wherein--.

Column 3, line 7, "$Rh_6(CO_{16}$" should be --$Rh_6(CO)_{16}$--.

Column 5, line 25, "his" should be --bis--.

Column 6, line 50, "70 g" should be --10 g--.

In Claim 1, column 7, line 13, "ms" should be --is--.

Signed and Sealed this

Twenty-fourth Day of October, 1995

Attest:

BRUCE LEHMAN

Attesting Officer

Commissioner of Patents and Trademarks